United States Patent
Almirall et al.

(10) Patent No.: US 9,752,966 B2
(45) Date of Patent: Sep. 5, 2017

(54) CRYOFOCUSED SAMPLING OF VOLATILES FROM AIR USING PELTIER-ASSISTED CAPILLARY MICROEXTRACTION

(71) Applicants: Jose Almirall, Miami, FL (US); Anamary Tarifa, Miami, FL (US)

(72) Inventors: Jose Almirall, Miami, FL (US); Anamary Tarifa, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/246,866

(22) Filed: Aug. 25, 2016

(65) Prior Publication Data

US 2016/0377512 A1   Dec. 29, 2016

(51) Int. Cl.
| | | |
|---|---|---|
| *G01N 1/24* | (2006.01) | |
| *G01N 1/22* | (2006.01) | |
| *G01N 1/40* | (2006.01) | |
| *G01N 33/00* | (2006.01) | |
| *H01J 49/00* | (2006.01) | |
| *H01J 49/04* | (2006.01) | |
| *G01N 30/06* | (2006.01) | |
| *G01N 30/12* | (2006.01) | |

(52) U.S. Cl.
CPC .............. *G01N 1/24* (2013.01); *G01N 1/2273* (2013.01); *G01N 1/405* (2013.01); *G01N 33/0047* (2013.01); *H01J 49/0027* (2013.01); *H01J 49/0422* (2013.01); *H01J 49/0431* (2013.01); *G01N 2001/2229* (2013.01); *G01N 2001/2282* (2013.01); *G01N 2030/062* (2013.01); *G01N 2030/122* (2013.01)

(58) Field of Classification Search
CPC .................................................... G01N 1/2214

USPC ............ 73/864.34, 864.51, 864.71; 422/412, 422/501, 502
See application file for complete search history.

(56) References Cited

U.S. PATENT DOCUMENTS

| | | | |
|---|---|---|---|
| 9,267,866 B2 | 2/2016 | Almirall et al. | |
| 2007/0248500 A1* | 10/2007 | Pawliszyn | B01J 20/28014 422/400 |
| 2014/0260974 A1* | 9/2014 | Almirall | G01N 1/2035 95/90 |

OTHER PUBLICATIONS

Haddadi, S.H. et al., "Cold fiber solid-phase microextraction device based on thermoelectric cooling of metal fiber," *Journal of Chromatography A*, 2009, pp. 2783-2788, vol. 1216.

* cited by examiner

*Primary Examiner* — R. A. Smith
*Assistant Examiner* — John M Royston
(74) *Attorney, Agent, or Firm* — Saliwanchik, Lloyd & Eisenschenk

(57) ABSTRACT

A CMV sampling device includes a thermoelectric cooler, a vacuum pump, and one or more holders for one or more capillary microextractor of volatiles (CMV) tubes. The holder thermally contacts the thermoelectric cooler and the vacuum pump is fluidly connected to the CMV tube. The CMV device is useful for sampling of volatile organic compounds from air. The sampling can be carried out rapidly to achieve a sample within the CMV tube that may be placed into a thermal desorption unit (TDU) coupled to an inlet port for introduction of the volatiles into an analytical instrument, such as, a gas chromatograph (GC), an ion mobility spectrometer (IMS), a liquid chromatograph (LC), and/or a mass spectrometer (MS) for analysis of one or more volatiles.

10 Claims, 5 Drawing Sheets

CRYOFOCUSED SAMPLING OF VOLATILES FROM AIR USING PELTIER-ASSISTED CAPILLARY MICROEXTRACTION

This invention was made with government support under 1547734 awarded by the National Science Foundation. The government has certain rights in the invention.

BACKGROUND OF INVENTION

The detection of volatile organic compounds (VOCs) present in ambient air is of great concern to air quality monitoring programs because of the potential hazards to human health and the environment but also of interest to forensic scientists interested in detecting VOCs associated with, for example, explosives, drugs, and ignitable liquid residues. The list of VOCs thought to be toxic organic compounds is extensive and has been compiled by the Environmental Protection Agency (EPA) to indicate chemicals of concern that may be detectable in areas where air pollution is present, such as industrial sites. While the severity of the hazard of different contaminants varies, many VOCs present in ambient air have the potential to act as mutagens and carcinogens. Therefore, unequivocal detection and quantitation of VOCs is important to managing and mitigating health impacts from toxic compounds. In an effort to address this issue, the EPA has published the "Compendium of Methods for Toxic Organic Air Pollutants" since 1984 (TO-13 to TO-17). These are a series of reports describing the most current methods and guidelines to be followed for the monitoring of VOCs in ambient air or polluted environments.

The analysis of VOCs in ambient air is currently performed with sorbent tubes following the guidelines from the EPA method TO-17. The commercially available sorbent tubes consist of a thin cylinder that can be made out of glass or stainless steel. The interior of the tubes are packed with sorbent material, thus the name sorbent tubes. Commonly used sorbent materials include: several variations of Tenax®, Carbotrap®, and Carbopack™, with the possibility of using multiple sorbents in a single tube. The sorbent material selected depends largely on the target compounds, specifically the volatility or vapor pressure of the molecule of interest. Each sorbent material is classified according to its strength, which is described as the affinity of the compounds to the sorbent. A strong sorbent will allow greater sampling volumes for all or most of the targeted VOCs and the strength of a sorbent tube is related to the surface area of the sorbent material. A weak sorbent has a surface area less than 50 $m^2/g$ (e.g. Tenax® TA), a medium sorbent has a surface area in the range of 100-500 $m^2/g$ and a strong sorbent has a surface area around 1000 $m^2/g$. In general, stronger sorbents are used for highly volatile compounds.

Some of the limitations observed for the analysis of VOCs with sorbent tubes include: long headspace extraction times (~1 hr) with low flow rates and the use of expensive thermal desorption units coupled to gas chromatography-mass spectrometry (GC-MS) through the use of transfer lines that can result in poor recoveries.

A capillary microextractor of volatiles (CMV) device, which can be a tube, is an extraction method for the detection of VOCs in forensic and environmental applications, as taught in Almirall et al. U.S. Pat. No. 9,267,866 Feb. 23, 2016. The CMV method has been demonstrated to result in improved sensitivity and selectivity compared to SPME, for the extraction of volatiles in the headspace of smokeless powders. Furthermore, it has also been shown to be effective for the detection of gunshot residues on swab samples from the hands of shooters. A standard CMV consists of an open-ended 2 cm glass capillary tube packed with vinyl terminated polydimethylsiloxane (PDMS) coated glass filters, as shown in FIG. 1. The inner diameter of the glass capillary is 2 mm and is packed with approximately seven strips (2 cm×2 mm) of the PDMS coated glass fibers. PDMS is a non-polar polymer that provides a hydrophobic coating over the glass filter, thus improving extraction of VOCs in humid conditions.

The use of PDMS has been demonstrated to be more effective than Tenax® TA for the analysis of large injection volumes and retention efficiency with good precision. With a total surface area of ~0.05 $m^2$ in the sampling device and a phase volume of 100 $mm^3$ for the CMV, the device offers greater absorption capacity compared to SPME where the surface area is $10^{-5}$ $m^2$ and phase volume is only 0.612 $mm^3$, improving the capacity of CMV over SPME by 5,000 times. It also facilitates dynamic sampling, thus increasing sampling efficiency and decreasing sampling time. A method to further enhance the efficiency of CMV is desired. Yet, further improvements to the degree of volatility and the quantity absorbed is desirable.

BRIEF SUMMARY

An embodiment of the invention is directed to a CMV sampling device, which includes a thermoelectric cooler, a vacuum pump, and at least one holder for a capillary microextractor of volatiles (CMV) tube and at least one CMV tube. The thermoelectric cooler thermally contacts the holder and the CMV tube, and the vacuum pump is fluidly connected to the CMV tube. The CMV tube can have a polydimethylsiloxane (PDMS) gel on glass fibers within a glass tube. The thermoelectric cooler can be a single-stage, dual-stage, or multi-stage Peltier cooler.

Another embodiment of the invention is a method for sampling volatile organic compounds from air, where the CMV sampling device is used to cool the CMV tube with an air stream being drawn through the CMV tube for a prescribed period of time. Air flow and cooling can be maintained for a period of 1 to 10 minutes at a temperature of −15 to 5° C.

Another embodiment of the invention is a method for analyzing volatile organic compounds from air, where a sample acquired by the sampling volatile organic compounds from air in a CMV tube is placed into and heated in a thermal desorption unit (TDU) that is coupled to an inlet port of an analytical instrument, such as a gas chromatograph (GC), an ion mobility spectrometer (IMS), a liquid chromatograph (LC), and/or a mass spectrometer (MS).

DETAILED DISCLOSURE

Figure 1:
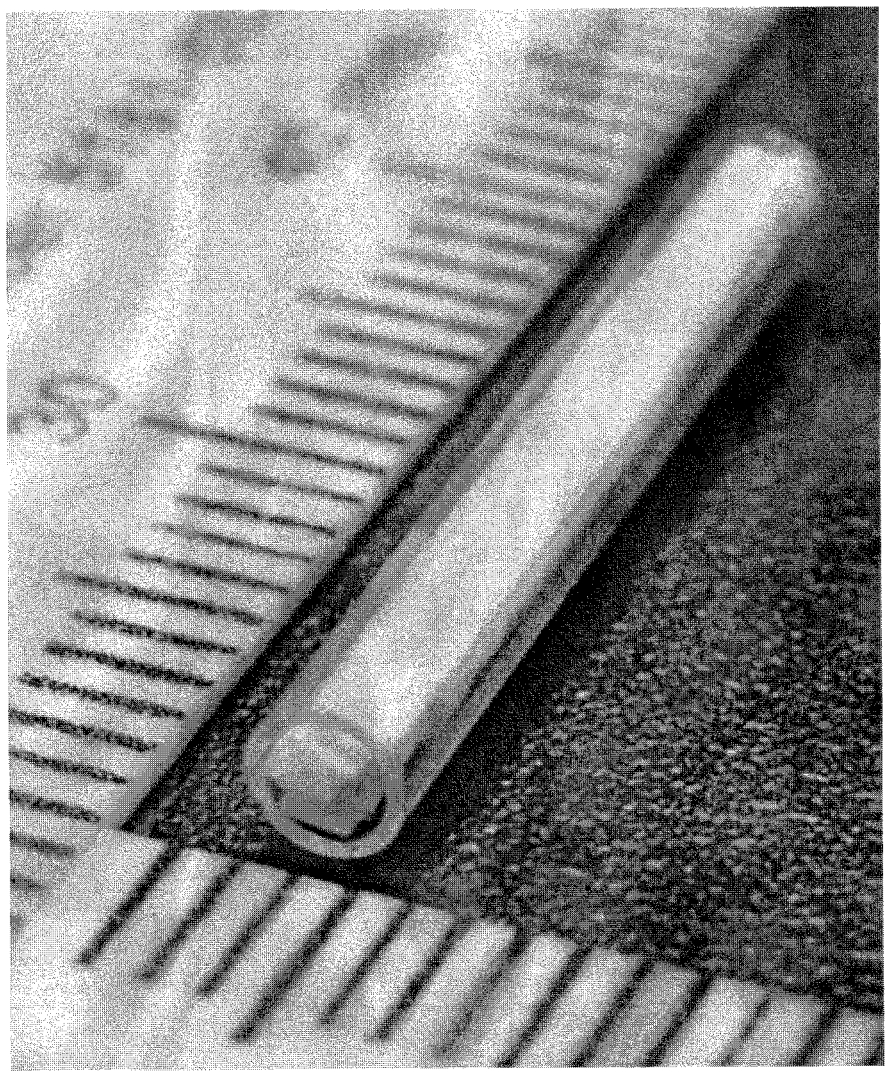
FIG. 1 shows a prior art capillary microextractor of volatiles (CMV) tube that is employed in the CMV device, according to an embodiment of the invention.
Figure 2A:
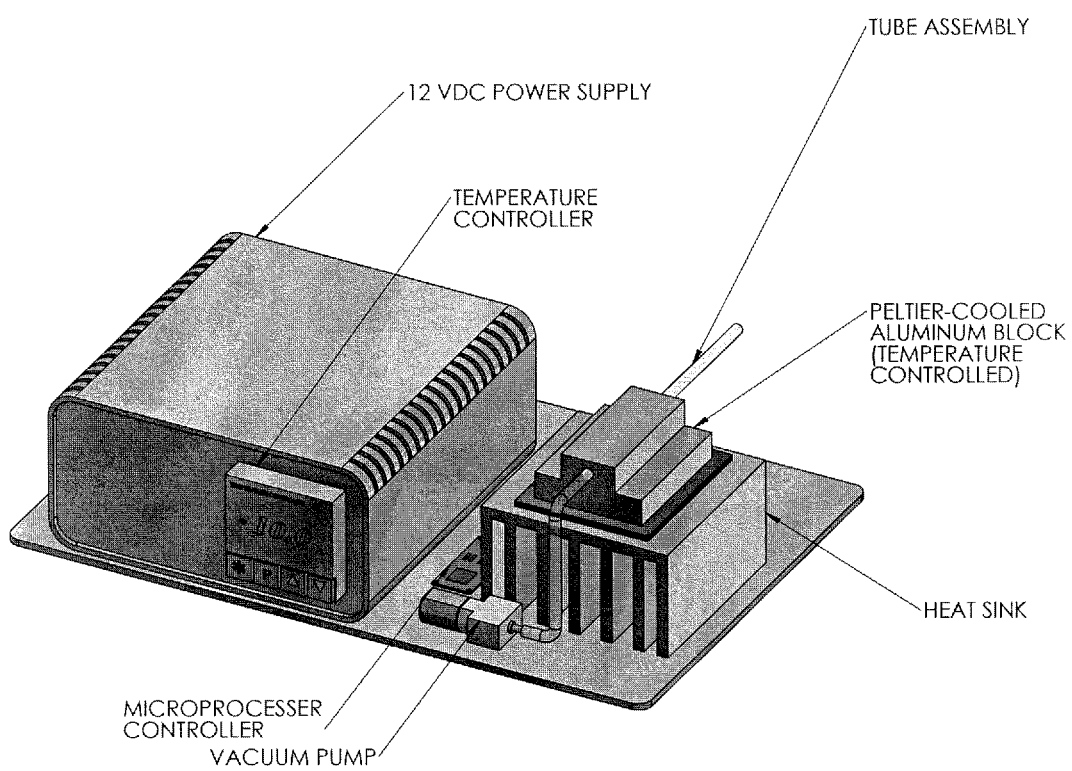
FIG. 2A shows a single-stage Peltier-cooled cryofocusing CMV device that includes temperature controller, according to an embodiment of the invention.
Figure 2B:
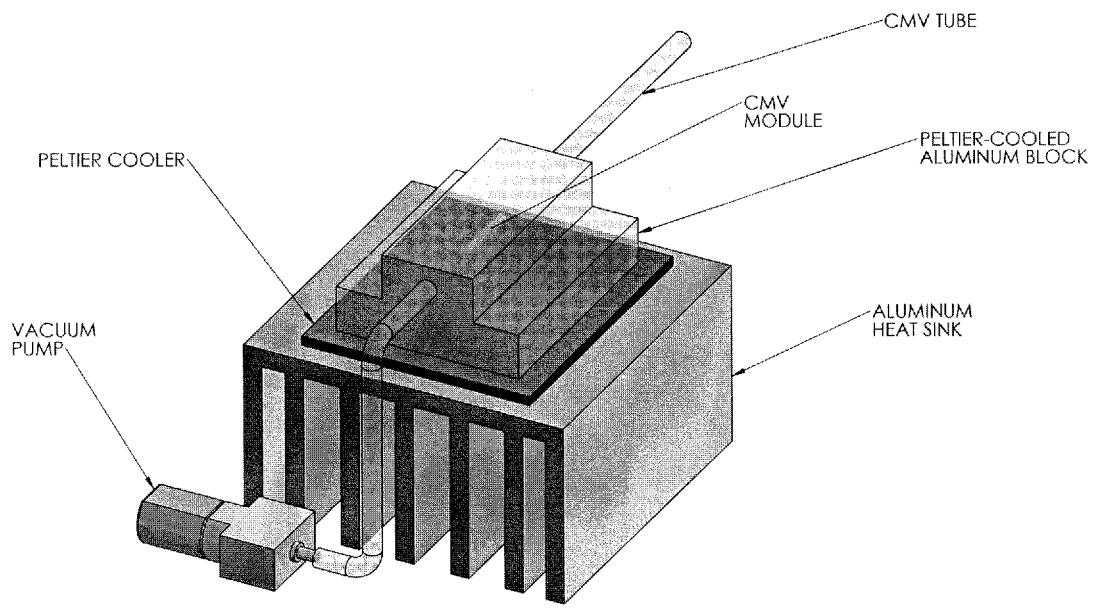
FIG. 2B shows a CMV module connected to the sampling CMV tube inserted into a holder thermally in communication with a Peltier-cooled aluminum block of the controlled device of FIG. 2A, according to an embodiment of the invention.

An embodiment of the invention is a method of improving the extraction of highly volatile compounds by a cryofocusing CMV technique with cooling of a CMV tube to −10° C. during a dynamic extraction using a Peltier-cooled module with a temperature controller as shown in FIGS. 2A and 2B. Although thermoelectric devices have been reported for the preconcentration of analytes using a cold fiber SPME, as disclosed in Haddadi et al. *J Chroma. A* 1216 (2009) 2783-88, and cooling assisted liquid extractions and thin film microextractions Haynes, CRC Handbook of Chemistry and Physics, ninety-sixth ed. (Internet Version 2016), W. M. Haynes, ed., CRC Press/Taylor and Francis, Boca Raton, 2016, the cooling of a gas stream through the absorbing medium is presented herein. CMV tubes are described in Almirall et al. U.S. Pat. No. 9,267,866 Feb. 23, 2016, which is incorporated herein in its entirety. The CMV tube consists of a housing containing an absorbent for the diagnostic volatiles and orifices that permit contacting of a gas suspected of containing the diagnostic volatiles. The absorbent can be a polydimethylsiloxane (PDMS) gel and can be a film on a partitioned support, such as glass fibers.

A CMV device is illustrated in FIG. 2A and FIG. 2B showing the use of a single stage Peltier-cooler, a single holder for the CMV tube, and a single CMV tube. In embodiments of the invention, a plurality of holders and CMV tubes can be used and a Peltier-cooler with a plurality of stages can be used to simultaneously to acquire a plurality of samples and to cool to temperatures that are below that which is readily achieved with a single stage Peltier-cooler. The sampling method can be performed for a prescribed period of 10 minutes or less, for example 1, 2, 3, 4, 5, 6, 7, 8, 9 or 10 minutes. The sampling method can be performed for a prescribed temperature of 10° C. or less, for example −15, −10, −5, −3.5, 0, 1, 2, 3, 4, 5, 6, 7, 8, 9, or 10° C.

The method, according to an embodiment of the invention, permits rapid extraction of VOCs in ambient air for CMV sampling that has superior performance relative to the performance according to the reported guidelines of the EPA method TO-17. The four performance criteria for the Compendium Method TO-17 are given as: method detection limit of 0.5 ppbv or less; analytical precision of 20%; precision for distributed volume pair of 25% or less; and audit accuracy within 30% for concentrations expected in contaminated ambient air (0.5 to 25 ppbv). In addition, the EPA TO-17 requires that the breakthrough of the sorbent tubes should be less than 5% during the sampling period. The superior performance of the CMV device with cryofocusing for use as a field sampling technique allow sampling of the headspace of indoor air, with many potential applications including forensic chemical analysis.

The cryofocused CMV method, according to an embodiment of the invention, facilitates rapid sampling and detection of VOCs using, for example, CMV-GC-MS. The cryofocused CMV method is fast and sensitive for headspace extraction of organic volatiles present in the air. One of the major advantages of CMV devices over sorbent tubes for air monitoring is the ability to conduct dynamic headspace sampling in less than 10 min by the cryofocused CMV method, compared to 1 hour using sorbent tubes. The CMV tube is cost efficient, being about one hundredth the cost of manufacture compared to sorbent tubes. The low cost facilitates disposable CMV sampling tubes, although CMV tubes may be reused after desorption in the GC injection port for more than 100 sample headspace extractions and injections, which is comparable to sorbent tubes such as Tenax® TA. Furthermore, the CMV can be directly introduced into the injection port of the GC using a low-cost thermal separation probe. The advantages of direct injection in the GC port include reduced sample loss and faster elution relative to other thermal desorption units that use a transfer line.

The cryofocused CMV method, according to an embodiment of the invention, for extraction of volatile organic compounds in ambient air meets the criteria described in the EPA method TO-17, depending on the analyzed compound. All tested compounds were found to meet the four method criteria specified in the EPA method TO-17 for all compounds tested with except of benzonitrile, nonanal, and acetophenone.

In an embodiment of the invention, a cryofocusing CMV device consists of a single-stage Peltier cooled module for cooling the CMV device to −10° C. during extraction. Breakthrough is improved for all compounds and remained similar for methylene chloride, toluene, and naphthalene. The cryofocusing CMV device employing CMV tubes provides extraction capabilities that permit analysis of highly volatile small molecules. The cryofocused CMV method, according to an embodiment of the invention, can be used for analysis of explosives in air and for the analysis of organic GSR from the hands of shooters. Additional forensic applications for cryofocusing CMV headspace extraction include detection of VOCs from fire debris, either from collected samples collected in a can or directly at the scene of a fire, in order to detect VOCs associated with the presence of ignitable liquid residues that may suggest the cause of the fire, including arson.

Methods and Materials

Materials

Standard compounds for 17 hazardous air contaminants (Table 1) were sourced from Fisher Scientific (Pittsburgh, Pa.), Sigma-Aldrich (St. Louis, Mo.), TCI America (Tokyo, Japan), Acros (New Jersey, USA), and Aldrich (Milwaukee, Wis.). Purities of stock standards exceeded 97.0% with the exception of 1,2,3-trimethylbenzene (90.0%), benzonitrile (95.0%), and nonanal (95.0%). A 300 ng µL-1 mixture of the standard compounds was prepared in methanol and stored in a 10 mL amber glass vial (Fisher Scientific, Pittsburgh, Pa.). The standard mixture solution was further diluted to concentrations ranging from 1.0 to 250 ng $\mu L^{-1}$

Fabrication of the Cryofocusing Device

Figure 3:
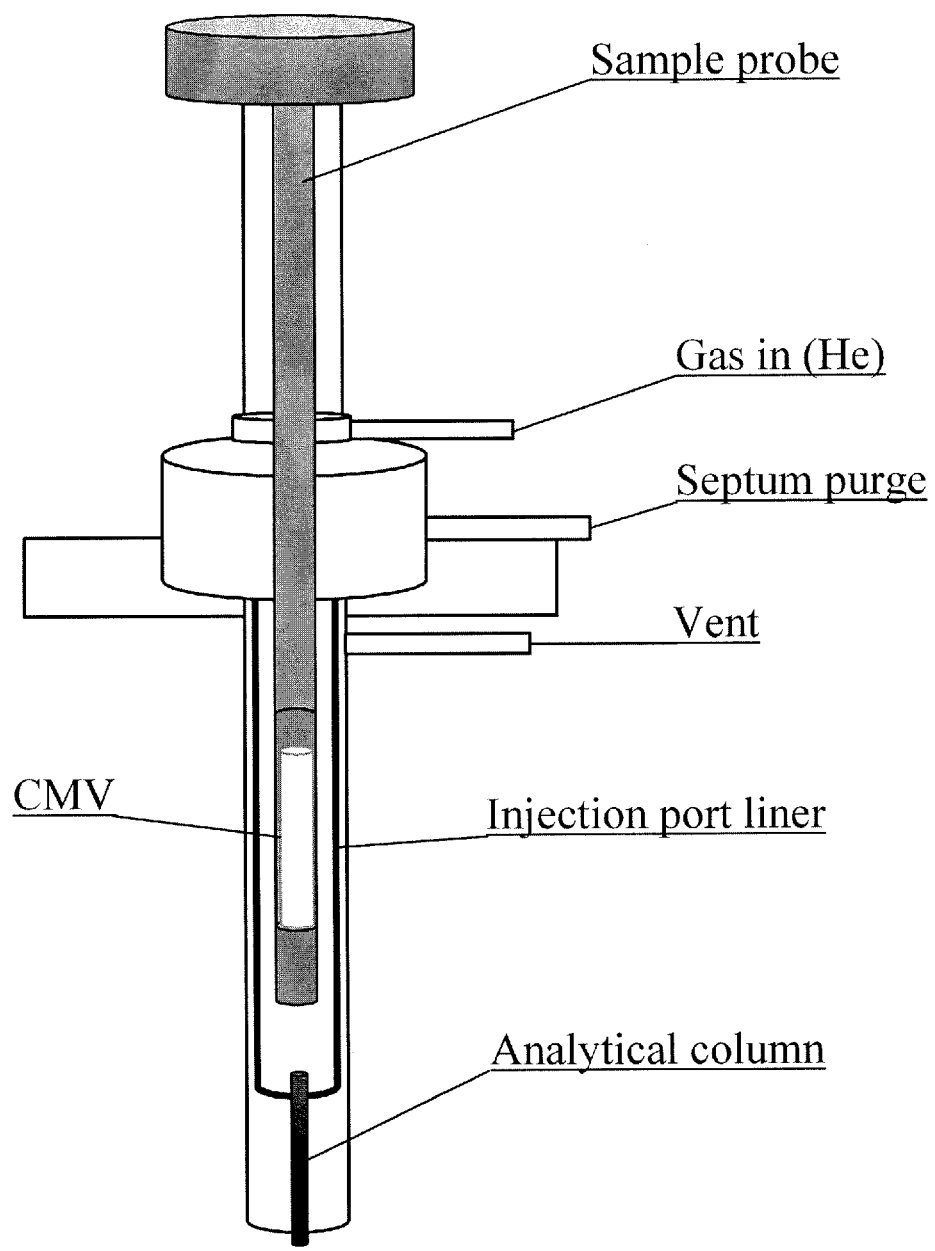
FIG. 3 shows a schematic of the CMV tube inserted in the injection port of a GC using a thermal separation probe.

A 5V single-stage Peltier-cooled thermoelectric cooler and heat sink assembly (Adafruit, New York, N.Y.) was attached to an aluminum block on the cold surface and the heat sink and fan, on the hot surface and configured with a thermocouple probe and orifice large enough to fit the CMV tube, as shown in FIGS. 2A and 2B. A small vacuum pump, capable of drawing 1 L/min, was used to sample the air through the CMV device. A commercially available thermal separation probe (Agilent, Santa Clara, Calif.) was used to insert the CMV into the inlet port, as shown in FIG. 3, of the GC-MS (Agilent, Santa Clara, Calif.).

Instrumentation

All analyses were conducted using a 7890A gas chromatogram coupled to a 5975C inert XL MSD with a triple axis detector (Agilent Technologies, Santa Clara, Calif.). The CMV was introduced directly into the GC injection port for thermal desorption using an Agilent Thermal Separation Probe (TSP) with a Sky® 4mm ID single taper inlet liner (Restek, Bellefonte, Pa.). A schematic of the TSP with the CMV in the injection port of the GC system is shown in FIG. 3.

A 29.17 m×0.25 mm×0.25 µm DB-5 ms Ultra Inert column (Agilent Technologies, Santa Clara, Calif.) was used for chromatographic separation. The GC oven ramp temperature started at 35° C. with a 1 min hold. The oven was then ramped to 120° C. at 15° C./min, to 220° C. at 30° C./min with a 1.5 min hold, and subsequently to a final temperature of 280° C. at 30 ° C./min with a 1 min hold. The total time for the chromatographic separation was 14.50 min.

The injector temperature was set at 180° C. in split mode (split ratio 5:1) with a column flow of 1.2 mL/min. The EI source was kept at 230° C., the transfer line to the mass spectrometer was set to 280° C. and the quadrupoles were maintained at 150° C. The scan mass range was set at 45-300 amu. The resolution of the mass analyzer is 0.1 amu. The instrument was tuned before each experiment using the autotune feature as recommended by the manufacturer.

A list of the target compounds with their respective retention times and ion peaks is presented in Table 1, below, and used to confirm the presence of the presence of the target compounds in the field samples.

TABLE 1

Compound list in order of elution time ($t_R$) for the headspace extraction at 20° C. The quantifier and qualifier ions, method limits of detection (MDL), method quantitation limits (MQL), and precision (as % RSD, n = 3) for both direct spike onto a CMV and the headspace extraction using CMV and % recoveries for the headspace extraction using the CMV.

| Compounds | $t_R$ min | Quantifier ion | Qualifions ions Q1 | Q2 | Direct spike on CMV MDL ng | MQL ng | % RSD | Headspace extraction with CMV MDL ng | MQL ng | % RSD | % Recovery |
|---|---|---|---|---|---|---|---|---|---|---|---|
| Methylene chloride | 2.61 | 84 | 49 | 86 | 4.1 | 14 | 25 | $10^b$ | $30^b$ | $23^c$ | $2.7^c$ |
| Benzene | 3.44 | 78 | 77 | 51 | 4.6 | 15 | 19 | 37 | 123 | 13 | 11 |
| Pyridine | 4.35 | 79 | 52 | 78 | 3.3 | 11 | 13 | $60^b$ | $187^b$ | $38^c$ | $10^c$ |
| Toluene | 4.54 | 91 | 92 | 65 | 2.9 | 10 | 23 | 17 | 55 | 25 | 18 |
| Furfural | 5.31 | 96 | 95 | 39 | 3.7 | 12 | 15 | 74 | 247 | 30 | 8.0 |
| Ethylbenzene | 5.67 | 91 | 106 | 77 | 2.0 | 6.6 | 11 | 33 | 110 | 7 | 26 |
| m-Xylene/p-Xylene | 5.77 | 91 | 106 | 77 | 3.0 | 10 | 15 | 23 | 75 | 15 | 18 |
| o-Xylene | 6.05 | 91 | 106 | 105 | 2.9 | 10 | 12 | 24 | 81 | 14 | 17 |
| Benzaldehyde | 6.87 | 105 | 106 | 77 | 2.5 | 8.4 | 12 | 52 | 173 | 20 | 16 |
| Phenol | 6.92 | 94 | 66 | 65 | 3.1 | 10 | 15 | $2.2^b$ | $6.1^b$ | $23^c$ | $0.6^c$ |
| Benzonitrile | 7.09 | 103 | 76 | 50 | 2.6 | 8.8 | 14 | 53 | 177 | 16 | 11 |
| 1,2,4-Trimethylbenzene | 7.19 | 105 | 120 | 91 | 2.4 | 8.1 | 12 | 47 | 155 | 7 | 14 |
| 1,2,3-Trimethylbenzene | 7.47 | 105 | 120 | 91 | 2.6 | 8.7 | 14 | 88 | 292 | 4 | 12 |
| Acetophenone | 7.88 | 105 | 77 | 120 | 2.8 | 9.3 | 11 | 83 | 276 | 29 | 4.5 |
| Nonanal | 8.15 | 57 | 67 | 81 | 5.6 | 19 | 9 | 95 | 315 | 33 | 1.2 |
| Naphthalene | 8.88 | 128 | 127 | 102 | 2.5 | 8.4 | 12 | 56 | 186 | 15 | 11 |

[a] Precision in the calibration curve at 15 ng (direct spike) and 200 ng (headspace), % Recovery from headspace extraction at 200 ng.
[b] MDL and MQL for this compounds were calculated as stated in the EPA method TO-17.
[c] Precision (% RSD) and % Recovery were calculated for these compounds at 500 ppm.

Method Development

Prior to sampling, conditioning of the CMV was performed in an oven at 250° C. for 30 min. The CMV was then desorbed as a blank sample in the GC-MS. Liquid standards containing a known mass of the analytes were spiked (1 µL) directly onto the CMV and thermally desorbed in the GC inlet, as indicated in FIG. 3. The headspace extraction of VOCs was performed using a portable vacuum pump connected to a flow meter and capable of a sampling rate of 0.2 L/min. A 1 µL standard containing a known amount of the target analyte(s) was spiked onto a Kimwipe (Kimberly-Clark Global Sales LLC, Roswell, Ga.) that was placed inside a pre-baked quart can (~0.95 L) (All-American Containers, Miami, Fla., USA) and sealed. All cans were previously baked to 250° C. in an oven over three days prior to use, to remove any volatile contaminants from the manufacturing process. Holes were fashioned on the can lids and sealed using a rubber septum (Capitol Scientific Inc. Austin, Tex.) to facilitate sampling through the holes. The extraction results are reported in total mass extracted (ng), with values for the headspace calibration curve reported as the calculated amount of mass extracted.

The evaluation of CMV devices using the EPA compendium TO-17 method was performed using the standard solutions with the following optimized parameters: 1 min equilibrium time, 10 min extraction time, 0.2 L/min sampling flow and total sampling volume of 2 L at a room temperature of 20° C. The headspace calibration curves were also constructed using those parameters.

Optimization of the method using the cryofocusing device at −10° C. was performed at different equilibrium times (30 mins and 3 hours) and different extraction times (15 sec, 30 sec, 1, 1.5, 2.5, 5, 10, 15, 20, 25, 30 mins) to determine recovery and volume extraction capability at a sampling flow of 0.2 L/min. The experiments showed that an equilibrium time of 30 min was suitable for the extraction of the compounds of interest and an extraction time of 10 min was optimum for most VOCs at a sampling flow of 0.2 L/min. Recovery experiments were performed at room temperature (20° C.) and using the cryofocusing device (−10° C.) with subambient conditions being more favorable for greater volume extraction.

Field Sampling

To demonstrate the utility of air monitoring in the field, triplicate samples were collected in a chemical laboratory, a lecture hall and a nail and hair salon. CMV's were conditioned and analyzed prior to field sampling to ensure no previous contamination or carryover. All samples were extracted for 10 min at a flow rate of 0.2 L/min, at 20° C. The chromatographic peaks in the samples were first identified using the NIST mass spectral reference library and confirmed by comparing the mass spectra of the individual standard compounds, under the same instrumental conditions.

Method Validation with CMV Devices

A rapid GC-MS temperature program (14.5 min) was developed for the detection of 17 volatile organic compounds commonly found in the air of polluted environments as indicated in Table 1, above, that represent a wide range of boiling points (40.0° C. to 217.9° C.). The retention time for each compound was determined by injecting 1 µL of a 20 ppm of the standard into the GCMS. Chromatographic separations were achieved for all the compounds except for m-xylene and p-xylene, therefore, a combined quantitation was used for these compounds. The parameters and performance of the developed method as an extraction technique for air sampling was established by following the criteria specified in the EPA TO-17. The criteria include method detection limit (MDL) of ≤0.5 ppbv (~3-5 ng), analytical precision of replicate measurements within 20%, precision for the distributed volume pair of 25% or less, and an audit accuracy of 30% or better for the expected concentration range 0.5-25 ppbv (5-300 ng).

Calibration curves for direct liquid injections into the GC, direct injection on the CMV, and headspace extraction were developed with the standard mixture across a range of 1 ppm to 300 ppm to correspond with the highest concentration of compounds that are commonly detected in polluted air. The linearity of the calibration curves was determined by plotting concentrations with a response of a signal-to-noise ratio (SNR) of 10 or larger. The linearity obtained for the calibration curves were greater than 0.925, 0.969, and 0.951 for direct liquid injection, direct spike on CMV, and headspace extraction, respectively. The percent recovery for headspace extraction using a 200 ng standard ranged from 2.7-26%, with the exception of phenol (0.6%) and nonanal (1.2%), as indicated in Table 1, above.

The sensitivity of the method was tested by determining the method detection limits (MDL) and the method quantitation limits (MQL) for all analytes by direct spike on CMV and by headspace extraction with the CMV device. Detection limits for each compound was determined using two methods. In the first method analysis of 10 replicates of a methanol blank sample was performed. The standard deviation of the integrated signal (or noise) at the known analyte retention times was multiplied by 3. The second method (described in EPA TO-17) consisted of conducting an analysis on 7 replicates at a concentration close to the expected MDL. The standard deviation of the replicates was multiplied by 3.14 (Student's t value for confidence interval of 99%). The mass detected for headspace MDL and MQL were calculated using the regression line results from the direct spike calibration curves.

Table 1 summarizes the MDL obtained for direct spike on the CMV and the headspace extraction. It is worth mentioning that the reported MDL in Table 1 for headspace extraction calibration curves represent the minimal sample concentration that can be spiked on a can for the signal-to-noise ratio (SNR) of the response to be at least 3. Calibration curves for headspace extraction of methylene chloride, pyridine, and phenol were not feasible due to their low detection requiring a spiked concentration of 500 ppm or more. Therefore, the MDL and MQL for these compounds were calculated using the second method described above.

As shown in Table 2, below, the breakthrough calculated was higher than that specified in the EPA TO-17 method (5%). The only compounds with similar breakthroughs were benzonitrile (7%) and naphthalene (5%). Nonetheless, the compounds were detected at the expected detection limits.

TABLE 2

Compound list in order of elution time (tR) for the headspace extraction at 20° C. The quantifier and qualifier ions, breakthrough (as %), analytical precision (n = 3), distributed volume pair (as %) and audit accuracy (as %) calculated following the EPA TO-17 for the headspace extraction with CMV.

| Compounds | $t_R$ min | Quantifier ion | Qualifier ions Q1 | Qualifier ions Q2 | Breakthrough % | Analytical Precision % | Distributed volume pair % | Accy % |
|---|---|---|---|---|---|---|---|---|
| Methylene chloride | 2.61 | 84 | 49 | 86 | | | | |
| Benzene | 3.44 | 78 | 77 | 51 | 46 | 15 | | 8.9 |
| Pyridine | 4.35 | 79 | 52 | 78 | | | | |
| Toluene | 4.54 | 91 | 92 | 65 | 35 | 20 | 12 | 8.2 |
| Furfural | 5.31 | 96 | 95 | 39 | | 4 | | 9.2 |

TABLE 2-continued

Compound list in order of elution time (tR) for the headspace extraction at 20° C. The quantifier and qualifier ions, breakthrough (as %), analytical precision (n = 3), distributed volume pair (as %) and audit accuracy (as %) calculated following the EPA TO-17 for the headspace extraction with CMV.

| Compounds | $t_R$ min | Quantifier ion | Qualifier ions Q1 | Qualifier ions Q2 | Breakthrough % | Analytical Precision % | Distributed volume pair % | Accy % |
|---|---|---|---|---|---|---|---|---|
| Ethylbenzene | 5.67 | 91 | 106 | 77 | 27 | 3 | 16 | 7.4 |
| m-Xylene/p-Xylene | 5.77 | 91 | 106 | 77 | 22 | 18 | 17 | 8.2 |
| o-Xylene | 6.05 | 91 | 106 | 105 | 21 | 14 | 11 | 8.3 |
| Benzaldehyde | 6.87 | 105 | 106 | 77 | 10 | 1 | 11 | 8.4 |
| Phenol | 6.92 | 94 | 66 | 65 | | | | |
| Benzonitrile | 7.09 | 103 | 76 | 50 | 7 | 2 | 36 | 8.9 |
| 1,2,4-Trimethylbenzene | 7.19 | 105 | 120 | 91 | 12 | 3 | 6 | 8.6 |
| 1,2,3-Trimethylbenzene | 7.47 | 105 | 120 | 91 | 15 | 3 | 10 | 8.8 |
| Acetophenone | 7.88 | 105 | 77 | 120 | 28 | 42 | 34 | 9.5 |
| Nonanal | 8.15 | 57 | 67 | 81 | 19 | 60 | 1.3 | 9.9 |
| Naphthalene | 8.88 | 128 | 127 | 102 | 5 | 18 | 10 | 8.9 |

$^a$Retention times ($t_R$), breakthrough at 0.2 L/min sampling rate for a 30 ng standard solution and, analytical precision in percent, precision for the distributed volume pair, and audit accuracy for a 200 ng standard solution. Values not reported are from concentrations below the method detection limit.

The analytical precision calculated demonstrates lower performance for acetophenone and nonanal. However, all other compounds have an analytical precision of 20% or less, as indicated in Table 2, above. The distributed volume pair precision is calculated by performing several measurements at different volumes. The amount (ng) of VOCs extracted at different sampling volumes and sampling flow (extraction time constant) should result in a linear response. For this purpose, two different sampling volumes (2 L and 3 L) were evaluated. The distributed volume pair precision obtained ranged from 1-36% for all compounds. Factors that can affect the precision are artifact formation, and breakthrough of the compounds. The compounds with distributed volume pairs higher than the expected (25%) were: benzonitrile and acetophenone. Finally, the % audit accuracy was less than the expected percentage value (30%) for the compounds. Calculations for % audit accuracy take into account the % recovery for each compound to properly represent the extraction efficiency of the CMV. All compounds were found to meet the four method criteria specified in the EPA method TO-17 except benzonitrile, nonanal, and acetophenone.

In order to improve the recovery and breakthrough of the target compounds, a thermoelectric cooler was constructed to accommodate the CMV devices and perform cryofocusing headspace extraction. The optimized extraction volume was determined by calculating the recovery at different extraction volumes at a constant sampling flow of 0.2 L/min, as indicated in Table 3, below.

Figure 4A:
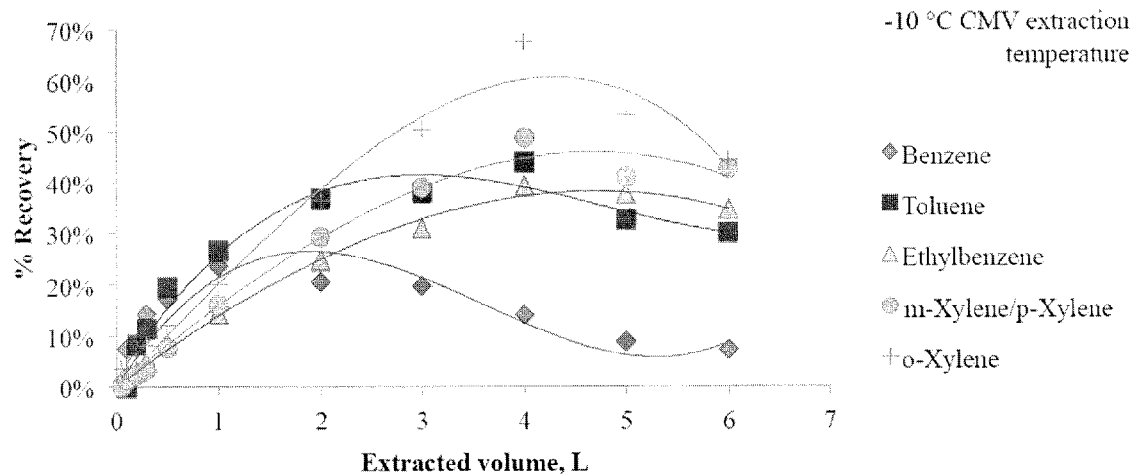
FIG. 4A is a composite of response curves for the % recovery of BTEX compounds at different extracted volumes at −10° C., according to an embodiment of the invention.
Figure 4B:
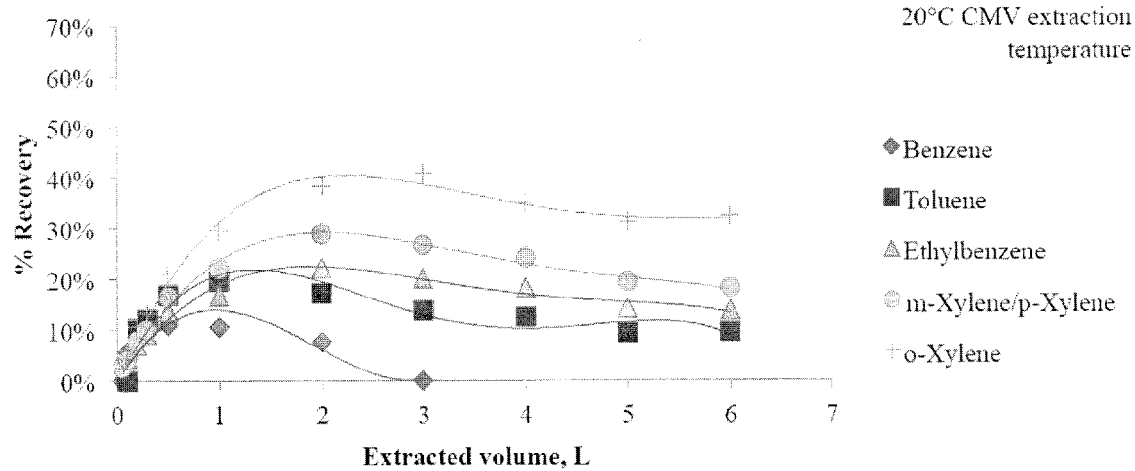
FIG. 4B is a composite of response curves for the % recovery of BTEX compounds at different extracted volumes at 20° C.

FIGS. 4A and 4B shows response curves of % recovery with different extracted volumes (0.05, 0.1, 0.2, 0.3, 0.5, 1, 2, 3, 4, 5, 6 L) sampled at −10° C., FIG. 4A, in comparison to the response curves at 20° C., FIG. 4B. The figure shows that, at the extraction temperature of −10° C., up to 4 L of sampling volume can be drawn through the CMV while recovering 14% or more for the BTEX compounds as well as for most detected compounds except benzonitrile (7%) and naphthalene (1%). A 2 L extraction volume, over 10 min. at a flow of 0.2 L/min. produced the optimal recovery of most compounds. An improvement between 35-100% in recovery resulted in the use of the lower temperature extraction.

Breakthrough experiments were also performed using the cryofocusing device operated at −10° C. and at room temperature (20° C.). Compared to room temperature results, the calculated breakthrough at −10° C. were generally lower for most compounds and no breakthrough was detected for the 30 ng spikes of phenol and benzonitrile. The use of a higher flow rate of (1 L/min) resulted in an increase in breakthrough and reduced recoveries, for some compounds. However, a sampling flow of 1 L/min at −10° C. favors the extraction of the compounds eluting after 6.8 mins, see Table 1, above.

TABLE 3

Compound list in order of elution time ($t_R$). The quantifier and qualifier ions, and recovery for headspace extraction with CMV devices at sampling flow of 0.2 L/min and 10 min extraction time at −10° C.

| Compounds | $t_R$ min | Quantifier ion | Qualifier ions Q1 | Qualifier ions Q2 | Recovery % |
|---|---|---|---|---|---|
| Methylene chloride | 2.61 | 84 | 49 | 86 | 21 |
| Benzene | 3.44 | 78 | 77 | 51 | 20 |
| Pyridine | 4.35 | 79 | 52 | 78 | |
| Toluene | 4.54 | 91 | 92 | 65 | 37 |
| Furfural | 5.31 | 96 | 95 | 39 | |
| Ethylbenzene | 5.67 | 91 | 106 | 77 | 25 |
| m-Xylene/p-Xylene | 5.77 | 91 | 106 | 77 | 29 |
| o-Xylene | 6.05 | 91 | 106 | 105 | 36 |
| Benzaldehyde | 6.87 | 105 | 106 | 77 | 8 |
| Phenol | 6.92 | 94 | 66 | 65 | |
| Benzonitrile | 7.09 | 103 | 76 | 50 | 3 |
| 1,2,4-Trimethylbenzene | 7.19 | 105 | 120 | 91 | 19 |
| 1,2,3-Trimethylbenzene | 7.47 | 105 | 120 | 91 | 8 |
| Acetophenone | 7.88 | 105 | 77 | 120 | 2 |
| Nonanal | 8.15 | 57 | 67 | 81 | 5 |
| Naphthalene | 8.88 | 128 | 127 | 102 | 1 |

Dynamic Headspace Sampling of Indoor Air with CMV

As a proof of concept, indoor air samples were collected using the optimized parameters: sampling flow rate (0.2 L/min) and 10 min extraction time. Three replicates of indoor air samples were extracted from different rooms including a laboratory (918 ft$^2$), a classroom (1694 ft$^2$), and a nail and hair salon (1053 ft$^2$). The extraction in the laboratory was performed in one half of the room. The portable pump and the CMV were placed on top of a table and the CMV was positioned in an upward direction for the 10 min extraction time. The air extraction in the classroom was performed in one of the corners of the room. The air extraction in the hair and nail salon was performed towards the middle of the room between the hair and nail sections. All replicates were performed in the same location for each room.

Figure 5A:
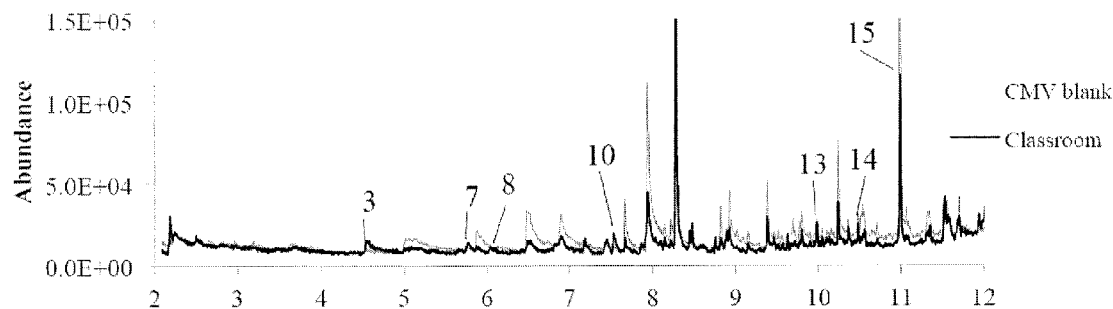
FIG. 5A shows a GC trace of CMV-GC-MS analysis showing the compounds identified in a classroom where the peaks are from the group: (1) acetone; (2) ethyl acetate; (3) toluene; (4) ethyl methacrylate; (5) butyl ester acetic acid; (6) 1-chloro-4-(trifluoromethyl)benzene; (7) m, p-xylenes; (8) o-xylene; (9) benzaldehyde; (10) limonene; (11) camphor; (12) tridecane; (13) tetradecane; (14) pentadecane; (15) diethyl phthalate.
Figure 5B:
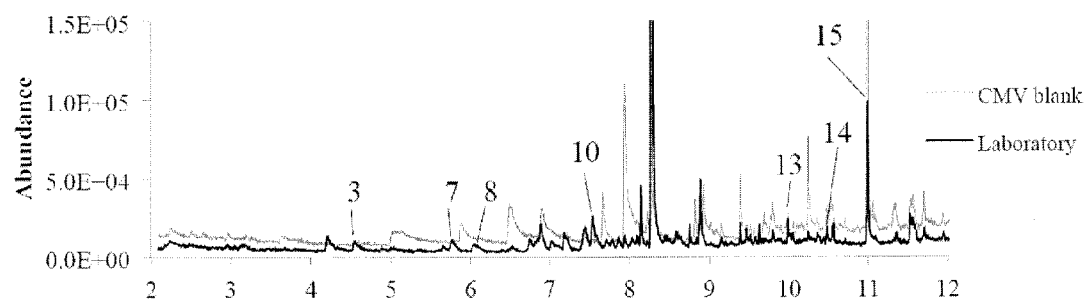
FIG. 5B shows a GC trace of CMV-GC-MS analysis showing the compounds identified in a laboratory where the peaks are from the group: (1) acetone; (2) ethyl acetate; (3) toluene; (4) ethyl methacrylate; (5) butyl ester acetic acid; (6) 1-chloro-4-(trifluoromethyl)benzene; (7) m, p-xylenes; (8) o-xylene; (9) benzaldehyde; (10) limonene; (11) camphor; (12) tridecane; (13) tetradecane; (14) pentadecane; (15) diethyl phthalate.
Figure 5C:
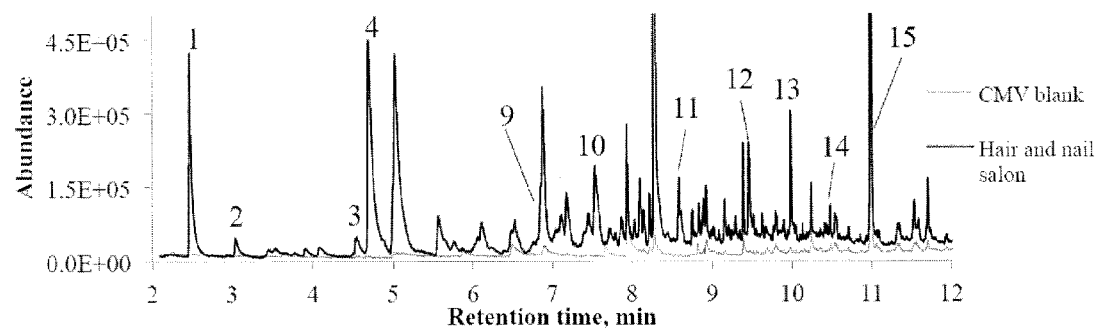
FIG. 5C shows a GC trace of CMV-GC-MS analysis showing the compounds identified in a hair and nail salon where the peaks are from the group: (1) acetone; (2) ethyl acetate; (3) toluene; (4) ethyl methacrylate; (5) butyl ester acetic acid; (6) 1-chloro-4-(trifluoromethyl)benzene; (7) m, p-xylenes; (8) o-xylene; (9) benzaldehyde; (10) limonene; (11) camphor; (12) tridecane; (13) tetradecane; (14) pentadecane; (15) diethyl phthalate.

The extraction was performed at room temperature (~21.0° C.). An example of the chromatograms obtained from the three different rooms is shown in FIGS. 5A, 5B, and 5C. The compounds identified in the chromatograms were detected at least in two of the three replicates obtained from each room. Compounds of interest are Peak identities: acetone; ethyl acetate; toluene; ethyl methacrylate; butyl ester acetic acid; 1-chloro-4-(trifluoromethyl)benzene; m, p-xylenes; o-xylene; benzaldehyde; limonene; camphor; tridecane; tetradecane; pentadecane; and diethyl phthalate. From the compounds calibrated in this study, toluene, m, p-xylenes and o-xylenes were detected below the MQL in the laboratory and the classroom. In the hair salon, the amount of toluene detected was 6.5 ng. According to the Occupational Safety & Health Administration (OSHA), the permissible exposure limit for toluene is 10 ppm (37 $mg/m^3$), which is orders of magnitude higher than the amount detected in the nail salon.

The presence of other compounds detected in the samples including hexane, camphor, tridecane, tetradecane, pentadecane, and diethyl phthalate were confirmed by obtaining the retention time and mass spectrum of a 10 ppm standard solution. Quantitation of these compounds was not conducted. Other compounds such as acetone, ethyl acetate, ethyl methacrylate, butyl ester acetic acid, 1-chloro-4-(trifluoromethyl)benzene, and limonene were identified using the mass spectra by comparison with the NIST library. Presence of acetone in nail salon is expected since this is the main ingredient of nail polish remover. Ethyl acetate, ethyl methacrylate, and butyl ester acetic acid are also ingredients of nail polish, acrylic nails, and acrylic removers. In addition, 1-chloro-4-(trifluoromethyl)benzene is used as a solvent in commercial surface finishes. Limonene is a common monoterpene, detected in indoor air and is found in products such as, citrus fruits, air refresheners, household cleaning agents, hair dye, and waxes.

All patents and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A CMV sampling device, comprising a thermoelectric cooler, a vacuum pump, and at least one holder for a capillary microextractor of volatiles (CMV) tube and at least one CMV tube, wherein the thermoelectric cooler thermally contacts the holder, and wherein the vacuum pump is fluidly connected to the CMV tube.

2. The CMV sampling device according to claim 1, wherein the CMV tube comprises a polydimethylsiloxane (PDMS) gel on glass fibers within a glass tube.

3. The CMV sampling device according to claim 1, further comprising an aluminum block as a heat sink.

4. The CMV sampling device according to claim 1, wherein the vacuum pump can draw 1 L/min.

5. The CMV sampling device according to claim 1, wherein the thermoelectric cooler is a single stage Peltier cooler.

6. A method for the sampling of volatile organic compounds from air, comprising:
   providing a CMV sampling device comprising at least one capillary microextractor of volatiles (CMV) tube fluidly connected to a vacuum pump and at least one holder for the (CMV) tube thermally contacting a thermoelectric cooler;
   powering the vacuum pump to produce an air flow of the air of a site suspected of containing a target volatile organic compound through the CMV tube; cooling the at least one holder and the at least one CMV tube to a temperature below the ambient temperature of the air; and
   maintaining the air flow and the cooling for a prescribed period of time.

7. The method of claim 6, wherein the air flow and cooling is maintained for a period of 1 to 10 minutes.

8. The method of claim 6, wherein the temperature is −15 to 5° C.

9. A method for analyzing volatile organic compounds from air, comprising:
   acquiring a sample according to the method of claim 6;
   placing the CMV tube into a thermal desorption unit (TDU);
   coupling the TDU to an inlet port of an instrument for analysis of a volatile; and
   heating the TDU to a temperature sufficient for desorbing the diagnostic volatile from the CMV, wherein the diagnostic volatile is introduced into the instrument for analysis of a volatile.

10. The method of claim 9, wherein the instrument for analysis of a volatile comprises a gas chromatograph (GC), an ion mobility spectrometer (IMS), a liquid chromatograph (LC), a mass spectrometer (MS), or any combination thereof.

* * * * *